United States Patent [19]

Schlossman et al.

[11] Patent Number: 5,219,997

[45] Date of Patent: * Jun. 15, 1993

[54] MONOCLONAL ANTIBODY WHICH INHIBITS THE ADHESION FUNCTIONS OF THE β INTEGRIN, CR3

[75] Inventors: Stuart F. Schlossman, Newton Centre; James D. Griffin, Sherbon, both of Mass.

[73] Assignee: Dana-Farber Cancer Institute, Boston, Mass.

[*] Notice: The portion of the term of this patent subsequent to May 28, 2008 has been disclaimed.

[21] Appl. No.: 703,941

[22] Filed: May 22, 1991

Related U.S. Application Data

[63] Continuation of Ser. No. 165,024, Mar. 7, 1988, Pat. No. 5,019,648, which is a continuation-in-part of Ser. No. 70,257, Jul. 6, 1987, abandoned.

[51] Int. Cl.$^5$ ............ C12P 21/08; C07K 15/28
[52] U.S. Cl. ............ 530/388.7; 530/388.73; 530/388.75; 530/388.22
[58] Field of Search ............ 530/380, 388.1, 388.2, 530/388.22, 388.23, 388.85, 395, 403, 388.7

[56] References Cited

U.S. PATENT DOCUMENTS 4,840,793  6/1989  Todd et al. ............ 424/85.8
5,019,648  5/1991  Schlossman et al. ............ 530/387

OTHER PUBLICATIONS

N. L. Letvin, et al., Blood 61(2): 408–410 (1983), Conservation of Myeloid Surface Antigens on Primate Granulocytes.

N. Dana et al. (I), J. Immunol. 137: 3259–3263 (Nov. 15, 1986), Two Functional Domains in the Phagocyte Membrane Glycoprotein Mo1 Identified with Monoclonal Antibodies.

N. Dana et al. (II), J. Immunol. 138: 3549–3554 (May 10, 1987), A Dysfunctional Mo1 Glycoprotein is Present on a Subline of the KG1 Acute Myelogeneous Leukemia Cell Line.

M. A. Arnaout et al., Fed. Proc. 44(10): 2664–2670 (Jul., 1985), Deficiency of Two Human Leykocyte Surface Membrane Glycoproteins Mo1 and LFA-2.

M. A. Arnaout et al., J. Clinc. Invest. 72(1): 171–179 (1983), Inhibition of Phagocytosis . . . By Monoclonal Antibodies to a Monocyte–Granulocyte Membrane Glycoprotein.

R. F. Todd III et al., Hybridoma (3): 329–337 (1982), Differentiation Antigens Mo1 and Mo2 on Human Monocytes.

R. F. Todd III et al., J. Clin. Invest. 74: 1280–1290 (1984), Subcellular Localization of Mo1 . . . A surface Glycoprotein Associated With Neutrophil Adhesion.

A. A. TeVelde et al., Chem. Abstr. 104: 500 (No. 184712d) (1986).

R. F. Todd et al., J. Immunol. 126(4): 1435–1442 (1981), Antigens on Human Monocytes Identified By Monoclonal Antibodies.

Huu et al., Immunology 62: 61–67 (1987), Comparison of Blocking Effects of Monoclonal Antibodies Anti–Mo1 Alpha and Anti–LFA–1 Alpha or Human Neutrophil Functions.

N. Dana et al. (III), J. Clin. Invest. 73: 153–159 (1984), Deficiency of a Surface Membrane Glycoprotein (Mo1) in Man.

R. F. Todd III et al., "Human Myelomonocytic Differentiation Antigens . . . " in Leukocyte Typing, A. Bernard et al., eds (Springer-Verlag: New York, 1984), pp. 424–433.

J. D. Griffin et al., J. Clin. Invest. 68: 932–941 (1981), Expression of Myeloid Differentiation Antigens on Normal and Malignant Myeloid Cells.

*Primary Examiner*—Robert J. Hill, Jr.
*Assistant Examiner*—David L. Fitzgerald
*Attorney, Agent, or Firm*—Myron C. Cass

[57] ABSTRACT

A hybrid cell line is developed which produces a monoclonal antibody which binds to a unique antigenic site expressed on the surface of phagocytic cells. The monoclonal antibody binds to and activates a specific domain of the CD11b glycoprotein so as to inhibit adhesion dependent functions of the phagocytic cell, but it does not affect other phagocytic functions. This monoclonal antibody can be used as a reactant in an in vitro diagnostic immunoassay for detecting the unique antigenic site on the surface of normal human neutrophils.

1 Claim, No Drawings

MONOCLONAL ANTIBODY WHICH INHIBITS THE ADHESION FUNCTIONS OF THE β INTEGRIN, CR3

This invention was made with funded support of the U.S. Government under PHS Grant No. CA 36167.

RELATED APPLICATION

This application is a continuation of U.S. Ser. No. 165,024, filed Mar. 7, 1988, now U.S. Pat. No. 5,019,648 entitled MONOCLONAL ANTIBODY SPECIFIC FOR THE ADHESION FUNCTION DOMAIN OF A PHAGOCYTE CELL SURFACE PROTEIN, which in turn is a continuation-in-part of U.S. Ser. No. 070,257, filed Jul. 6, 1987 and entitled MONOCLONAL ANTIBODY SPECIFIC FOR THE ADHESION FUNCTION DOMAIN OF A PHAGOCYTE CELL SURFACE PROTEIN abandoned. This application is related to application U.S. Ser. No. 061,336, filed Jun. 11, 1987, entitled METHOD OF REDUCING TISSUE DAMAGE AT AN INFLAMMATORY SITE USING A MONOCLONAL ANTIBODY, now U.S. Pat. No. 4,840,793 and to U.S. Ser. No. 165,025, filed Mar. 7, 1988 and entitled METHOD OF REDUCING TISSUE DAMAGE AT AN INFLAMMATORY SITE USING A MONOCLONAL ANTIBODY, now U.S. Pat. No. 4,935,234. The applicants of this application also are co-applicants named in said related applications.

This invention relates to a hybridoma cell line producing a monoclonal antibody which binds to a specific antigenic site expressed on the surface of phagocytic cells. More particularly, this monoclonal antibody binds to and inactivates a specific domain of the CD11b glycoprotein whereby to inhibit adhesion-dependent functions of the phagocytic cell, albeit without affecting the other phagocyte functions.

BACKGROUND OF THE INVENTION

Peripheral blood in the circulatory system of a human is comprised principally of red blood cells, platelets, and white blood cells or leukocytes. The family of white blood cells is comprised of lymphocytes, neutrophils, monocytes, eosinophils, and basophils. Lymphocytes are of T cell or B cell subtypes primarily; additional subsets of lymphocytes are known also. The variety of functions of leukocytes and their clinical relevance has generated great interest in the scientific community.

Neutrophils, eosinophils, and basophils are identified as "granulocytes" because of their content of cytoplasmic granules. Granulocytes and monocytes are identified as "phagocytes" because of their ability to phagocytose or ingest bacteria, other micro-organisms and other types of foreign materials referred to generally as "antigens". This phagocytic function is important in defending the host against a variety of infections and further, is important in various types of inflammatory disorders. Phagocytes are produced from common progenitor cells in the bone marrow, circulate in the peripheral blood and finally, enter tissues as necessary for control of infection or for participating in an inflammatory reaction. Such response functions are found in human, and animal phagocytes, i.e., in primates and canines.

The neutrophil is the most common leukocyte in human and animal peripheral blood. One microliter of normal human whole blood includes, on average, $5 \times 10^3$ leukocytes, of which 3,975 are neutrophils, 150 are eosinophils, 25 are basophils, 250 are monocytes, and 1,500 are lymphocytes.

In the immunological response of granulocytes or monocytes to any type of infection of inflammation, these cells are first activated to migrate to the appropriate area in response to "chemo-attractant factors" such as certain bacterial products, complement components, etc. This attraction process is termed "chemotaxis". Once in an area of inflammation or infection, granulocytes and monocytes other undertake to establish a firm attachment to their targets. For this purpose, these cells possess a number of specific cell surface receptor glycoproteins that promote this interaction, such as complement, Fc, and fibronectin receptors.

One of the most important family of cell surface receptor glycoproteins involved in phagocyte adhesion is the leukocyte cell adhesion molecule family identified as Leu-Cam or CD11/CD18. This family is comprised of at least three cell surface proteins which have two subunits each. They share a common beta subunit, CD18, of 94,000 daltons molecular weight and have different alpha subunits. The known members of this family are termed LFA-1 (CD11a/CD18), Mo1 (CD11b/CD18), and P150, 94 (CD11c/CD18). These glycoproteins have alpha subunits of 180,000, 155,000 and 150,000 dalton molecular weight, respectively. Each of these cell surface proteins have been specifically identified through the use of monoclonal antibodies. The biological importance of this family of surface glycoproteins has been recognized through the identification of a human disease in which leukocytes are genetically deficient in this family of antigens. The disease is characterized by recurrent severe bacterial infections and deficiencies in adhesion-dependent functions, such as, phagocytosis, chemotaxis, leukoaggregation, and neutrophil spreading on plastic.

Mo1 is a cell surface glycoprotein present on granulocytes, mononuclear phagocytes and null cells (Todd, R. F. III, Nadler, L. M., and Schlossman, S. F., Antigens on human monocytes, *Journal of Immunology*, 126:1435–1442, 1981). In humans, this molecule consists of two non-covalently linked proteins of 155,000 and 94,000 daltons (Todd, R. F. III, van Agthoven, A., Schlossman, S. F., and Terhorst, D., Structure analysis of differentiation antigens Mo1 and Mo2 on human monocytes, *Hybridoma* 1:329–337, 1982). This complex has been shown to mediate cell adhesion to a variety of surfaces, including other granulocytes, endothelium, and inert substrates. Genetic deficiencies in these molecules result in recurrent bacterial infections due to the inability of granulocytes to mediate an anti-microbial inflammatory response. Patients who are deficient in these molecules are characterized by an elevated leukocyte count (called "leukocytosis") and functional defects in phagocyte activity as measured in vitro by reduced or absence of aggregation adhesion to substrates, chemotaxis, and phagocytosis of opsonized particles. Activation of granulocytes and monocytes by soluble inflammatory mediators increases expression of these molecules (Todd. R. F. III, Arnaout, M. A., Rosin, R. E., Crowley, C. A., Peters, W. A., and Babior, B. M. The subcellular localization of Mo1 (also described as Mo1 alpha, gp110, CD11b/CD18, Mac-1, OKM1 antigen, iC3b receptor, CR3), a surface glycoprotein associated with neutrophil adhesion, *J. Clin. Invest.*, 74:1280–1290, 1984; Arnaout, M. A., Hakim, R. M. Todd, R. F., Dana, N. and Colten, H. R. Increased expression of an adhesion-promotion surface glycoprotein in the granulocytopenia of hemodialysis. *New Engl. J. Med.*, 312:457-462, 1985). Monoclonal antibodies directed against the Mo1 glycoprotein effectively prevent neutrophil aggregation in vitro as well as prevent phagocytosis.

The Mo1 glycoprotein has been of particular interest because its molecular structure has the capacity to bind a component termed "iC3b", a fragment of the third component of complement (Arnaout, M. A., Todd, R. F. III, Dana N., Melamed, J., Schlossman, S. F., and Colten, H. R. Inhibition of phagocytosis of complement C3 or IgG-coated particles and of iC3b binding by monoclonal antibodies to a monocyte-granulocyte membrane glycoprotein (Mo1), *J. Clin. Invest.*, 72:171-179, 1983. Also, the Mo1 glycoprotein is critically important in all of the adhesion-dependent phagocyte functions. Different monoclonal antibodies have been shown to inhibit the functions of the Mo1 glycoprotein.

The monoclonal antibody derived from the novel hybrid cell line embodying the invention is capable of inhibiting the adhesion-dependent function of neutrophils, but does not bind the iC3b fragment of the third component of complement. This monoclonal antibody is identified by the designation "MY904". It binds to specific antigenic sites of neutrophils, i.e. to the antigenic site on the CD11b/CD18 phagocyte surface protein which is specifically involved in granulocyte adhesion. The addition of the MY904 monoclonal antibody to phagocytes will thus inhibit adhesion-dependent phagocyte functions; but it does not inhibit other functions of either the CD11b/CD18 molecule, such as binding of complement component iC3b, or other types of neutrophil or monocyte functions, such as Fc receptor activation, activation of the respiratory burst by chemotactic peptide or phorbol diester and others.

The utility for such a site specific monoclonal antibody is very diversified. The binding of the MY904 monoclonal antibody to the adhesion dependant domain of neutrophils could specifically inhibit neutrophil migration to an area of inflammation or infection. In addition, such binding to neutrophils could inhibit adhesion and spreading of activated neutrophils already within such an inflammatory or infected site and then block release of toxic substances by the neutrophils. The monoclonal antibody MY904 could be labelled with a suitable marker for immunoassay of the CD11b/CD18 molecule or be conjugated to a suitable substrate for depletion of bound cells by fluorescence activated cell sorting or magnetic bead separation. The ability of the MY904 monoclonal antibody to block certain phagocyte functions would have special utility for in depth study of phagocyte function, especially where excess or harmful phagocyte function is involved in clinical disorder. Further, this monoclonal antibody is useful for quantitating surface expression of CD11b/CD18 and thereby can be applied to diagnose the Mo1 deficiency disease described herein.

SUMMARY OF THE INVENTION

A hybrid cell line which produces a monoclonal antibody specific for the adhesion-dependent domain of the Mo1 antigen expressed on the surface of human and animal phagocytes. The monoclonal antibody is specific for the part of the CD11b/CD18 phagocyte cell surface protein involved in adhesion of neutrophils and monocytes, and thus, the monoclonal antibody blocks adhesion-dependent phagocyte functions, such as chemotaxis and phagocytosis to an inflammatory or infection site without affecting certain other phagocyte functions thereof.

The monoclonal antibody is produced by a hybrid cell line in which one of the fusion partners was immunized to human chronic granulocyte leukemia cells.

PREFERRED EMBODIMENT OF THE INVENTION

The monoclonal antibody of the invention is identified by the designation MY904. It was developed from the fusion of mouse spleen cells immunized with purified chronic granulocytic leukemia (CGL) and mouse myeloma cells by a standard procedure described by Kohler and Milstein, *Nature* 256:495-497 (1975).

The human CGL cells used in the immunization procedure were unique and specifically prepared. Blood was obtained by venipuncture from a single patient with CGL in the blast phase for routine diagnostic studies. Mononuclear cells were prepared by Ficoll-Hypaque gradient density sedimentation, 1.077 g/cc. The mononuclear cells were then cryopreserved in 10% dimethylsulfoxide in the vapor phase of liquid nitrogen until used. For immunization, aliquots of the CGL cells were thawed, suspended in phosphate buffered saline (PBS), and $10 \times 10^6$ cells were injected into the peritoneal cavity and subcutaneous areas of a Balb/c mouse. This procedure was repeated at weekly intervals for one month. After an additional period of one month, the mouse was boosted with $10 \times 10^6$ cells from the same patient injected intravenously into a tail vein of the mouse. Three days later, the spleen of the mouse was recovered and the spleen cells harvested by conventional techniques.

The fusion to form hybridomas followed. The spleen cells were washed and mixed with the NS-1 plasmacytoma cell line at a ratio of eight spleen cells to the NS-1 cell in serum-free medium. The cells were centrifuged to pellet form and suspended in 0.5 ml of 30% polyethyleneglycol (PEG) for eight minutes at 25° C. The PEG was decanted, the cells diluted in hypoxanthine-aminoterin-thymidine media and distributed to microtiter plates. Tests for reactivity of the monoclonal antibody MY904 were performed by indirect immunofluorescence and flow cytometry, screening being for reactivity with CGL cells from the original patient. The MY904 monoclonal antibody was selected by virtue of this reactivity with the immunizing CGL cells and lack of reactivity with normal human T lymphocytes and B lymphocytes.

The MY904 monoclonal antibody was shown to react with purified monocytes of 10/10 normal donors tested, 10/10 normal granulocytes tested, and 10/10 samples of normal bone marrow mononuclear cells. It did not react with purified B lymphocytes. Low antigen density was detected on a subset of peripheral blood large granular lymphocytes which had been shown to include the natural killer cells. The cell line KG-1 maintained in tissue culture was tested and shown to be positive for the MY904 epitope. The HL-60 and U937 myeloid cell lines were tested and shown to be negative, but if they are induced to differentiate in vitro by the addition of phorbol diester, both cell lines will then express the MY904 epitope. The following cell lines were tested and shown to be negative: K562, Daudi, Nalm-1, Nalm-6, JB, Raji, CEM, HSB, and 5 Epstein-Barr-transformed B lymphocyte cell lines (Laz-221, -388, -156, -471, -509). Normal erythrocytes and platelets lack expression of MY904, as do phytohemagglutinin-activated T lymphocytes.

Expression of the MY904 epitope on human leukemic cells was studied. The antibody reacts with granulocytes from all patients with stable phase chronic granulocytic leukemia (CGL). Thirty patients with the blast phase of chronic granulocytic leukemia were studied. The blast cells from 9 cases were positive. One hundred ninety-three cases of acute myeloblastic leukemia were studied; the MY904 monoclonal antibody reacted with leukemic cells of 56% of these patients.

The monoclonal antibody is of the IgG1 subclass and immunopreciptitates a glycoprotein composed of two subunits of 155,000 daltons and 94,000 daltons molecular weight from surface labelled normal human granulocytes (Dana, N., et al. Two functional domains in the phagocyte membrane glycoprotein Mo1 identified with monoclonal antibodies. *J. Immunol.* 137:3259-3263, 1986). The distribution of reactivity of monoclonal antibody MY904 does not inhibit iC3b binding, but it is a potent inhibitor of the adhesion-dependent processes, granulocyte spreading on plastic and chemotaxis. Dana et al., ibid. In comparison with other anti-Mo1 monoclonal antibodies, the MY904 monoclonal antibody was unique in that it inhibited only adhesion-dependent functions but not binding of iC3b. Other antibodies tested included monoclonal antibodies 44, 903, 94, 17, OKM10, and Leu-15. Dana et al., ibid.

Thus, monoclonal antibody MY904 identifies the Mo1 granulocyte/monocyte cell surface glycoprotein, and further binds specifically to an epitope on that glycoprotein which is involved in adhesion-dependent processes of granulocyte/monocyte activities.

A sample of the hybrid cell line capable of producing MY904 monoclonal antibodies is on deposit with the American Type Culture Collection, (A.T.C.C.) 12301 Parklawn Drive, Rockville, Md. 20852, as of Aug. 19, 1988 and is assigned A.T.C.C. No. HB 9510.

Studies in vitro have shown that human, canine and subhuman primate leukocytes have in common the Mo1 glycoprotein. Letvin, N. L., Todd, R. F. III, Palley, L. S., and Griffin, J. D. Conservation of the MY904 myeloid surface antigen on primate and canine granulocytes has been demonstrated (*Blood* 61:408-410, 1983). Also, binding of the MY904 monoclonal antibody to normal dog neutrophils has been shown to effectively inhibit neutrophil aggregation in vitro when stimulated with the phorbol ester PMA (Giger, U., Boxer, L. A., Simpson, P. A., Lucchesi, B. R., and Todd, R. F. III. Deficiency of leukocyte surface glycoproteins Mo1, LFA-1, and Leu-M5 in a dog with recurrent bacterial infection: an animal model. *Blood* 69: 1622-1630, 1987).

The MY904 monoclonal antibody is unique because of its exceptional specificity for the adhesion domain of the CD11b/CD18 phagocyte surface protein. Further, this antibody has the ability to completely inhibit phagocyte functions which require expression of this critical cell surface structure.

We claim:
1. The monoclonal antibody MY904 produced by the hybridoma cell line A.T.C.C. No. HB9510.

* * * * *

UNITED STATES PATENT AND TRADEMARK OFFICE
CERTIFICATE OF CORRECTION

PATENT NO. : 5,219,997
DATED : June 15, 1993
INVENTOR(S) : Stuart F. Schlossman and James D. Griffin It is certified that error appears in the above-indentified patent and that said Letters Patent is hereby corrected as shown below:

On the title page, item [54] and column 1, line 2, change

"$\beta$ INTEGRIN" to --$\beta$2 INTEGRIN--;

Column 2, line 5, change "of" to --or--;

line 11, change "other" to --then--;

Column 3, line 40, change "adhesion dependent"

to --adhesion-dependent--;

Column 4, line 43, change "aminoterin"

to --aminopterin--.

Signed and Sealed this

Fifteenth Day of February, 1994

Attest:

BRUCE LEHMAN

*Attesting Officer*  *Commissioner of Patents and Trademarks*